United States Patent [19]

Mechoulam et al.

[11] Patent Number: 5,618,955
[45] Date of Patent: Apr. 8, 1997

[54] FATTY ACID DERIVATIVES AND PHARMACEUTICAL COMPOSITIONS CONTAINING SAME

[75] Inventors: Raphael Mechoulam; Aviva Beuer; Lemir Hanus, all of Jerusalem, Israel; William A. Devane, Chevy Chase, Md.

[73] Assignee: Yissum Research Development Company of the Hebrew University of Jerusalem, Jerusalem, Israel

[21] Appl. No.: 446,706

[22] PCT Filed: Nov. 30, 1993

[86] PCT No.: PCT/US93/11625

§ 371 Date: Jul. 26, 1995

§ 102(e) Date: Jul. 26, 1995

[87] PCT Pub. No.: WO94/12466

PCT Pub. Date: Jun. 9, 1994

[30] Foreign Application Priority Data

Nov. 30, 1992 [IL] Israel .................................. 103932

[51] Int. Cl.$^6$ ................................................. C07C 233/00
[52] U.S. Cl. ................................................................ 554/66
[58] Field of Search .......................... 554/66; 514/613, 514/625, 627

[56] References Cited

U.S. PATENT DOCUMENTS 4,619,938 10/1986 Takahashi et al. .................... 514/356

OTHER PUBLICATIONS

Fride et al, Chemical Abstracts, vol. 118, #15, 1993.

Primary Examiner—Gary Geist
Assistant Examiner—Deborah D. Carr
Attorney, Agent, or Firm—Keck, Mahin & Cate

[57] ABSTRACT

Pure polyunsaturated fatty acid amides and their derivatives. These synthetically produced compounds are able to mimic naturally occuring anandamides in the brain and bind the cannabinoid receptor. The compounds exhibit physiological activity and are useful as active ingredients in pharmaceutical compositions for the treatment of inflammation, migraines, spasticity activity, glaucoma, multiple sclerosis. The active compounds can be provided in isotope-tagged form.

9 Claims, 9 Drawing Sheets

ARACHIDONYLETHANOLAMIDE (ANANDAMIDE)

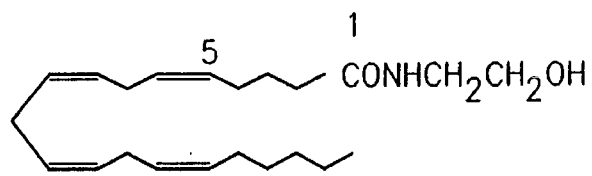
ARACHIDONYLETHANOLAMIDE (ANANDAMIDE)
FIG. 4A
$CH_3(CH_2)_{14}CONHCH_2CH_2OH$
PALMITYLETHANOLAMIDE
FIG. 4B
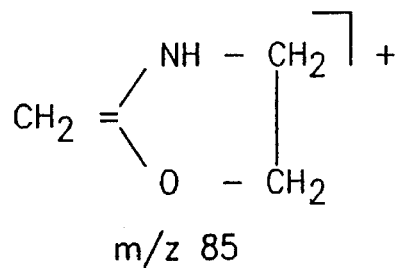
m/z 85
FIG. 4C
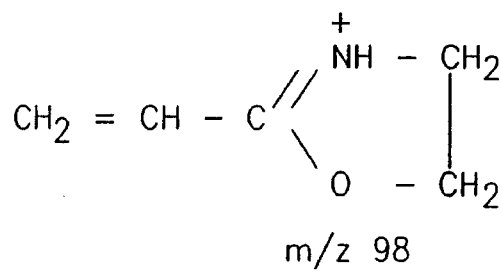
m/z 98
FIG. 4E
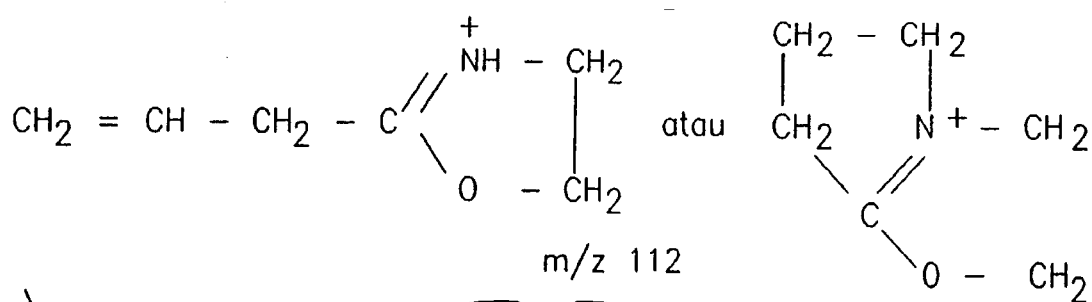
m/z 112
FIG. 4D

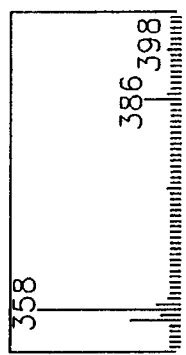
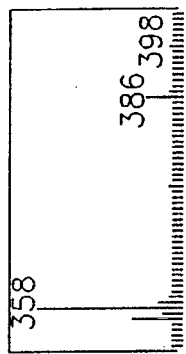
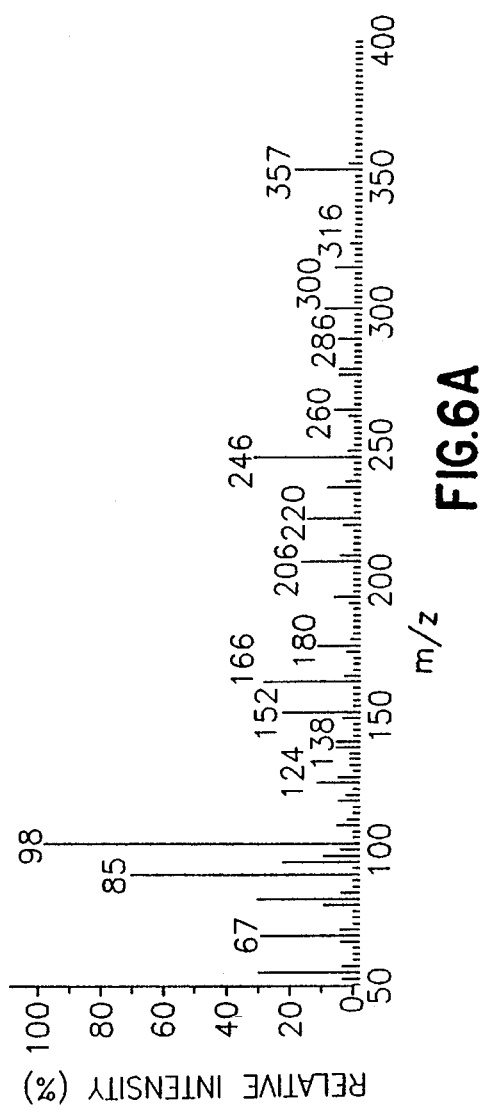
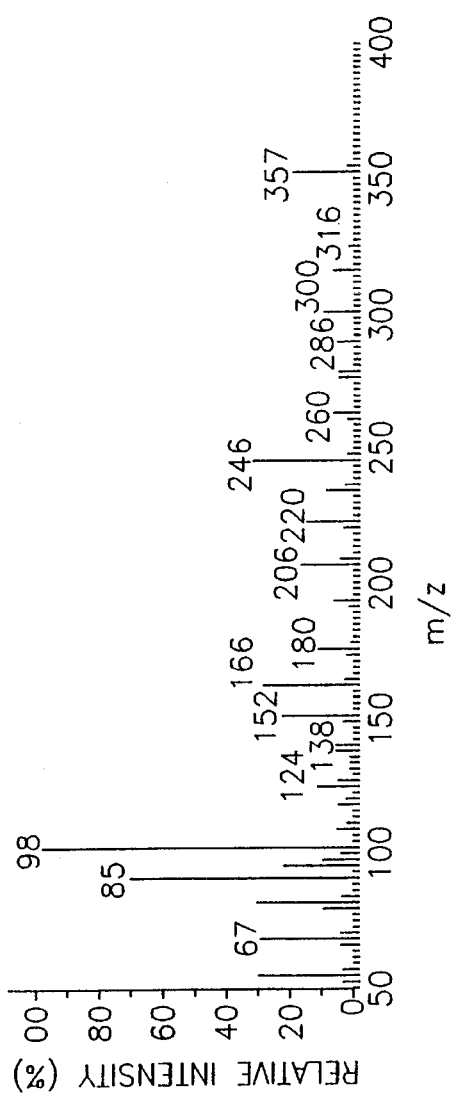

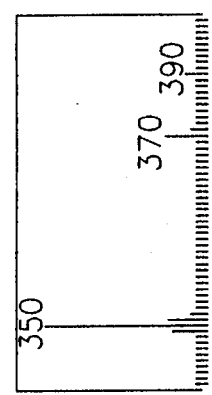
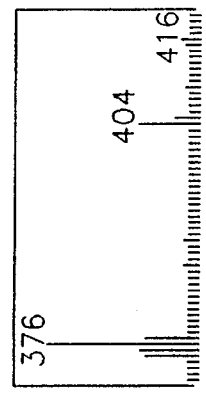
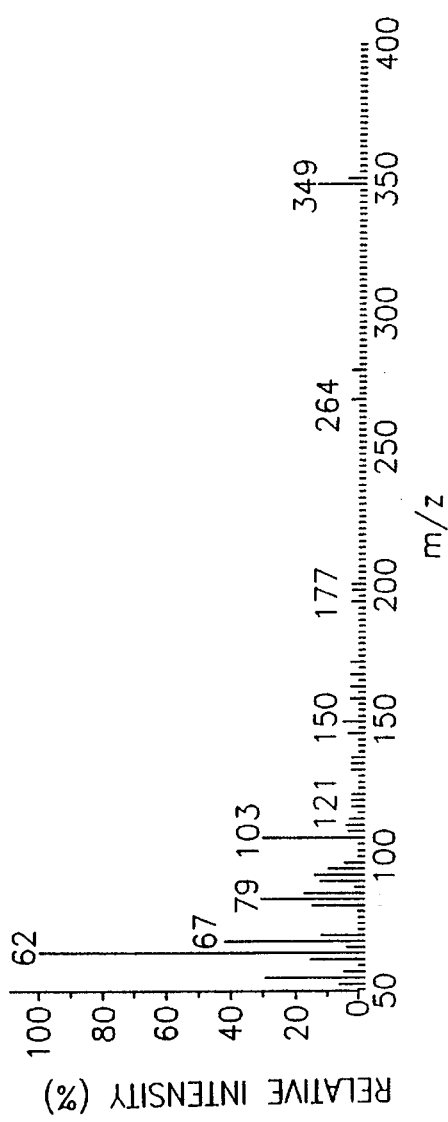
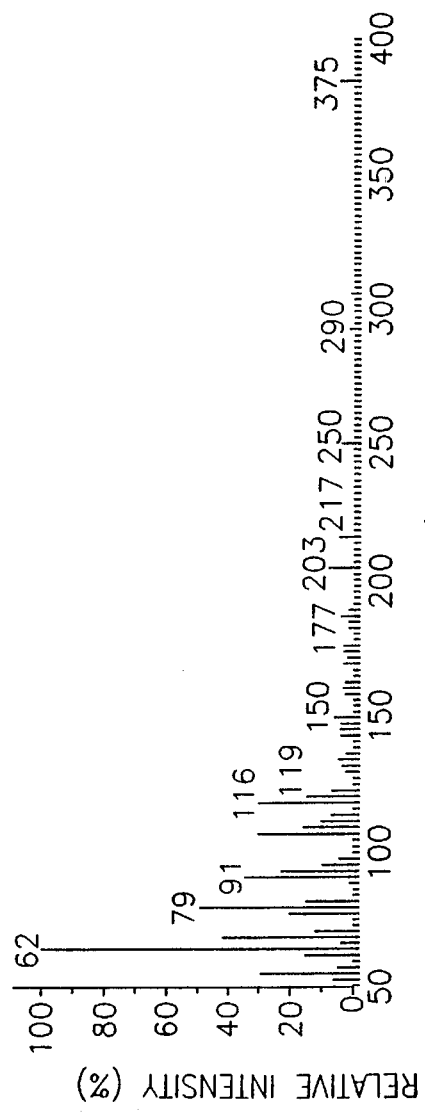

ANANDAMIDE
(1)

PALMITYLETHANOLAMIDE
(2)

LINOLENYLETHANOLAMIDE
(3)

LINOLENYLETHANOLAMIDE
(4)

HOMO-γ-LINOLENYLETHANOLAMIDE
(5)

DOCOSATETRAENYLETHANOLAMIDE
(6)

FATTY ACID DERIVATIVES AND PHARMACEUTICAL COMPOSITIONS CONTAINING SAME

This appln is a 371 of PCT/US93/11625 filed Nov. 30, 1993.

FIELD OF THE INVENTION

The invention relates to certain polyunsaturated fatty acid amides, and derivatives of these. Part of these are present in the brain, and part are products of synthesis. The novel pure compounds have a variety of pharmacological properties. They inhibit the specific binding of a cannabinoid probe to synaptosomal membranes. The compounds of the invention can be provided in radioactivity tagged form.

BACKGROUND OF THE INVENTION

Arachidonic acid ethanolamide (anandamide) and similar compounds are constituents of the brain. Anandamide and certain of the compounds similar with same, bind to the cannabinoid receptor. The binding of the ananamide to the cannabinoid receptor is similar to the binding of $\Delta^9$-tetrahydrocannabinol. There exist in the body many mediators, which are derivatives of arachidonic acid, such as prostaglandins and leukotrienes, which are present as large families of related compounds. Certain of these do not bind to the cannabinoid receptor, and it was one of the aims of the present invention to provide and identify compounds which have pharmacological properties similar to the properties of anandamide.

The existence of a receptor and the high structural requirements for cannabinoid activity indicate the possible presence of a specific endogenous cannabinoid ligand.

SUMMARY OF THE INVENTION

Endogenous ligands for the cannabinoid receptor have not yet been identified. Arachidonylethanolamide, a new arachidonic acid derivative—named anandamide, was isolated from porcine brain. Its structure was determined by mass spectrometry and nuclear magnetic resonance spectroscopy and was confirmed by synthesis. It inhibits the specific binding of a labelled cannabinoid probe to synaptosomal membranes in a manner typical of competitive ligands, and produces a concentration-dependent inhibition of the electrically-evoked twitch response of the mouse vas deferens, a characteristic effect of psychotropic cannabinoids. Similar compounds were synthesized and their pharma-cological properties were investigated.

$\Delta^9$-Tetrahydrocannabinol ($\Delta^9$-THC), the psychoactive constituent of Cannabis binds to a specific G-protein coupled receptor in the brain. Although the cannabinoid receptor in the rat and in the human has been cloned, its physiological function is unknown. The well established behavioral effects of THC and the abundance and anatomical localization of the receptor in the brain suggest a role for the receptor in the control of movement, memory, emotions and pain modulation, amongst other activities.

DESCRIPTION OF PREFERRED EMBODIMENTS

The existence of a receptor and the high structural requirements for cannabinoid activity indicate the possible presence of a specific endogenous cannabinoid ligand.

To screen for endogenous cannabinoid compounds there were tested brain-derived fractions using a centrifugation radioligand binding assay. Tritiated HU-243 (11-hydroxy-hexahydrocannabinol-3-dimethylheptyl homolog) with a $K_D$ of 45 pM in rat synaptosomal membranes, was used as the probe. Organic soluble extracts of porcin brain were first chromatographed according to standard protocols for the separation of lipids. Pig brains were homogenized in chloroform and/or methanol and centrifuged at 13,000 x g. The organic soluble extract was fractionated over silica (Kieselgel 60, 70–230 mesh), following elution schemes used to separate the major classes of lipids [C. C. Sweeley, *Methods Enzymol.* 14, 254 (1969); J. C. Dittmer and M. A. Wells, ibid. p. 482]. Many of the initial fractions isolated from brain inhibited the binding of [$^3$H]HU-243 to the cannabinoid receptor. Particular attention was paid to the binding of [$^3$H]HU-243 to the siliconized polypropylene microfuge tubes in which the assay was conducted. Normally, about 15–20% of the added [$^3$H]HU-243 adheres to the microfuge tube, with the amount increasing slightly when unlabelled cannabinoid drugs displace the radioligand from the receptor. When monitoring the three-way equilibrium of [$^3$H]HU-243 among the synaptosomal receptors, the solution and the microfuge tube, we observed that all the crude brain fractions which inhibited the binding of [$^3$H]HU-243 to the receptors also inhibited the binding of the radioligand to the microfuge tube. Several promising fractions were purified using both low and medium pressure column chromatography as well as thin layer chromatography (tlc). A combination of normal phase and reverse phase systems was employed. Tlc: Rf 0.65 on an analyticial RP-18 plate (Merck), eluted with methanol-dichloromethane, 4:1: developed twice-first solvent front: 3.1 cm, second solvent front: 7.4 cm. [W. A. Devane, L. Hanus, Mechoulam, Proceed. 5th Nordic Neuroscience Meet., *Publ. Univ. Kuopio Med.* p. 198 (1991)]. Anandamide elutes from a silica column (Kieselgel 60, 40–63 um, Merck) with methanol:chloroform (2:98). It elutes from a reverse-phase column (RP-C, 40–63 μm, Sigma) with methanol:water (88:12).

A compound was recovered (0.6 mg from 4.5 kg of brain), named anandamide, which shows one spot on tlc and elutes mainly as one peak on gas chromatography (GC) using a mass spectrometer as a detector. Anandamide inhibits the specific binding of [$^3$H]HU-243 to synaptosomal membranes in a manner typical of competitive ligands with a $K_D$ of 52+1.8 nM (n=3) (FIG. 1). In this system the $K_D$ of $\Delta^9$-THC was 46+3 nM.

Results from previous experiments, in which we compared the inhibitory effects of the 1,1-dimethylheptyl homologs of (+)- and (–)-11-hydroxy-delta-8-tetrahydrocannabinol on the electrically-evoked twitch response of the mouse vas deferens, indicate that this preparation is suitable as a model for investigating the mode(s) of action of psychotropic cannabinoids. R. G. Pertwee, L. A. Stevenson, D. B. Elrick, R. Mechoulam, A. D. Corbett, *Brit. J. Pharmacol.* 105, 980 (1992). Anandamide produced a concentration-dependent inhibition of the twitch response (FIG. 2). The inhibition was not reversed by naloxone (300 nM). The levels of inhibition are comparable to those of binding to the receptor.

The structure of anandamide was established by mass spectrometry (MS) and nuclear magnetic resonance (NMR) spectroscopy. Additional data were obtained from the GC-MS and CID measurements of the trimethylsilyl (TMS) derivative of the material. The results suggest that anandamide is an ethanolamide of a tetraenic $C_{20}$ fatty acid.

Support for the above structure was found in the behavior of anandamide under GC-MS conditions.

Thermal dehydration gives rise to m/z 329 M+ ion upon electron ionization (EI) and to m/z 330 MH+ under Cl. Both self-Cl m/z 330 MH+ and m/z 329 M+ are formed under EI conditions in an ion trap instrument (FIG. 3). The fragmentation pattern of the dehydration products was similar in the low mass range of the EI mass spectra of both anandamide and palmitylethanolamide: m/z 85 (McLafferty rearrangement ion) and m/z 98 (product of a γ-cleavage) (FIG. 4). The EI mass spectrum of dehydrated palmitylethanolamide exhibits an m/z 112 ion corresponding to a δ-cleavage fragment. The absence of this ion in the EI mass spectrum obtained in the GC-MS analysis of anandamide suggests the presence of the first double bond in the tetraenic acid at position 5 (as in arachidony-lethanolamide which would not be expected to yield a -cleavage product) (FIG. 4).

$^1$H NMR spectra were recorded. The peaks attributed to double bond protons (δ, 5.30–5.45, mult) were coupled with those of protons which have the chemical shifts of doubly allylic ones (δ, 2.75–2.90, mult). Such doubly allylic protons are typical for numerous naturally occuring all-cis, nonconjugated, polyunsaturated fatty acids such as linoleic and arachidonic acids. Three pairs of protons were observed between δ2.01–2.27, which we attributed to 2 allylic methylene groups and 1 methylene group α to a carbonyl moiety. Only one methyl group was observed (0.88,t). The peaks observed for 2 protons at 3.42 (N—CH t), 2 protons at 3.72 (O—CH$_2$,t) and 2 protons at 2.20 (COCH$_2$, t) are similar in chemical shifts and spin coupling patterns to peaks observed in the NMR spectrum of synthetic palmitylethanolamide. The peaks for N—CH$_2$ and O—CH$_2$ were coupled.

A juxtaposition of the above analytical data led us to conclude that the structure of anandamide is that of arachidonyl ethanolamide [5,8,11,14-icosatetraenamide, (N,-2-hydroxyethyl)-(all-Z)] a novel chemical entity. This conclusion was confirmed by synthesis. Arachidonyl chloride, prepared from arachidonic acid and oxalyl chloride (21), in methylene chloride, was added at 0 degrees C., under a nitrogen athmosphere to ethanolamine (in a ten fold molar excess) in methylene chloride. After 15 min the reaction was washed with water, dried, and the product (ca 90% yield) was purified by silica column chromatography (eluted with 2% methanol in chloroform) to give archidonylethanolamide, an oil, in 97% purity (by GC-MS). Synthetic arachidonylethanolamide was identical with the product obtained on tlc (10), NMR (300 MHz) and GC-MS (retention time and fragmentation pattern) (FIG. 3). Synthetic anandamide binds to the cannabinoid receptor K$_f$=39 ±5.0 nM (n=3).

The novel purified compound anandamide seems to be present as brain constituent. It is possible that this compound is present as a complex with another compound or in any other form, but according to the present invention it has been established that the compound defined herein as ananamide is characterized by the properties set out herein. Similar compounds, defined herein, are characterized by essentially equivalent properties and are part of the present invention.

This invention also relates to tagged form of such compounds, which can be used in a variety of research projects and in assays.

The invention further relates to pharmaceutical compositions containing an effective quantity of one of the compounds defined herein.

Following the synthetic method described for arachidonylethanolamide, the ethanolamides of the following unsaturated fatty acids were prepared.

| Systematic Name | Trivial Name | Shorthand designation |
| --- | --- | --- |
| 9,12-octadecadienoic* | linoleic | 18:2 (n-6) |
| 6,9,12-octadecatrienoic | δ-linolenic | 18:3 (n-6) |
| 8,11,14-eicosatrienoic | homo-δ-linolenic | 20:3 (n-6) |
| 4,7,10,13,16-docosapentaenoic | — | 20:5 (n-6) |
| 9,12,15-octadecatrienoic | δ-linolenic | 18:3 (n-3) |
| 5,8,11,14,17-eicoisapentaenoic | — | 20:5 (n-3) |
| 4,7,10,13,16,19-docosahexaenoic | — | 22:6 (n-3) |
| 5,8,11-eicosatrienoic | — | 20:3 (n-9) |

*The double-bond configuration in each instance is cis.

These ethanol amide derivatives have antiinflammatory analgetic, antiglaucoma and antiemetic activity (see Biological Results). In order to obtain 14C labeled compounds of importance in biological studies the above described synthetic procedure was repeated with 14C-labeled arachidonic acid to give 14C-arachidonyl ethanolamide, 50 mCl/mmol. With $^3$H-arachidonic acid we obtained $^3$H-arachidonylethanol amide, 150 Ci/mmol. When we used 14C-labeled ethanolamide we obtained 14C-arachidonylethanolamide, 50 mCi/mmol.

Biological Results

Analgesia.

The novel compounds were tested in the standard hot plate test.

Represenatative results are presented in Table I. The compounds were dissolved in a detergent (Emulphor):ethanol:saline (5:5:90) and administered by intravenous injection in the tail vein with an injection volume of 0.1 ml/10 g of body weight.

Antiemetic Activity

The compounds also tested in pigeons against emesia caused by all antieoplastic drug (cisplatin) according to the method described in Feigenbaum et al., Eur. J. Pharmacol. 169, 159–165 (1989). Representative results are presented in Table I.

The compounds were dissolved as described above for the tests on analgesia, and administered subcutaneously. The injection volume was 1.0 ml/kg body weight.

Antiglaucoma Activity

The compounds were also tested for antiglaucoma activity in rabbits with stable glaucoma induced by δ-chymotrypsin injection into the eye as described in detail in R. Mechoulam et al., On the therapeutic possiblities of some cannabinoids in "The Therapeutic Potential of Marihuana" (eds S. Cohen. R. C. Stillman) Plenum Press, New York, 1975. pp. 35–48). The compounds were compared in activity to that of pilocarpine (a standard antiglaucoma drug) which at 0.01% aq. solution reduces the intraocular pressure (I.O.P.) and delays recovery to half time of the original I.O.P. about 30 hours.

The fatty acid ethanol amides administered to the eye in 0.1% solution were less active than pilocarpine and delayed recovery to half time of the original I.O.P between 2 and 10 hours.

The compounds were dissolved as described for analgesia and further diluted with saline to obtain the required concentration.

Antiinflammatory Activity

The compounds were tested by a method reported by W. Calhoun et al., Agents and Actions, 21, 306–a309 (1987). Water was substituted for mercury as the displacement medium. PAF (1.0 μg) or arachidonic acid (1.0 mg) dissolved in 50 μl of 5% ethanol in saline was injected s.c. into the plantar surface of the right hind paw of female mice (20–25 g). The mice were under ether anesthesia during this procedure. The volume of the right foot was measured to the level of the lateral malleous by water displacement before treatment and 15 min after PAF injection or 30 min after arachidonic injection. The change in paw volume was calculated for each mouse. The results for two of the tested ethanolamides are presented in Table II.

Dosage

The effective doses for humans are between 1–100 mg total daily dose, by injection or by oral administration.

TABLE I

Analgesia and Vomiting Reduction

| Compound | Analgesia $ED^=_{50}$ (mg/kg)- | Reduction of vomiting (50%)$^=$ (mg/kg) |
|---|---|---|
| Arachidonylethanolamide | 4.2 | 2.5 |
| 5,8,11,14,17-eicosapentaenyl ethanolamide | 5.2 | 3.6 |
| 4,7,10,13,16,19-docosahexaenylethanolamide | 6.1 | 4.8 |
| 5,8,11-eicosatrienyl-ethanolamide | 7.6 | 6.2 |

⁻in mice. For details of administration see Text
⁼in pigeons. For details of administration see Text.

TABLE II

Inhibition of Arachidonic Acid-Induced Paw Edema-$^=$

| Dose (mg/kg)$^b$ | Arachidonyl-ethanolamide | 4,7,10,13,16,19 Docosahexaenyl ethanolamide |
|---|---|---|
| 0.010 | 56.2 | — |
| 0.025 | 58.4 | — |
| 0.050 | 74.2 | 52.4 |
| 0.100 | 98.0 | 66.8 |
| 0.250 | 100.0 | 72.0 |

$^=$Values shown are percent inhibition of paw edema when compared to vehicle treated controls. 95% significance by ANOVA. N = 5 mice/group.
$^b$Control mice were given peanut oil (50 μl) orally. Paw volume increase = 38 + 4 μl.

BRIEF DESCRIPTION OF THE FIGURES

The invention is illustrated with reference to the enclosed Figures, wherein:

FIG. 4 illustrates the structure of some compounds described;

FIG. 6 EI GC-MS spectra of dehydrated docosatetraenylethanolamine, Compound (6);

FIG. 7 EI GC-MS spectra of homo-δ-linolenylethanolamine (5) and of docosatetraenylethanolamine, (top and bottom);

LEGENDS

Figure 1:
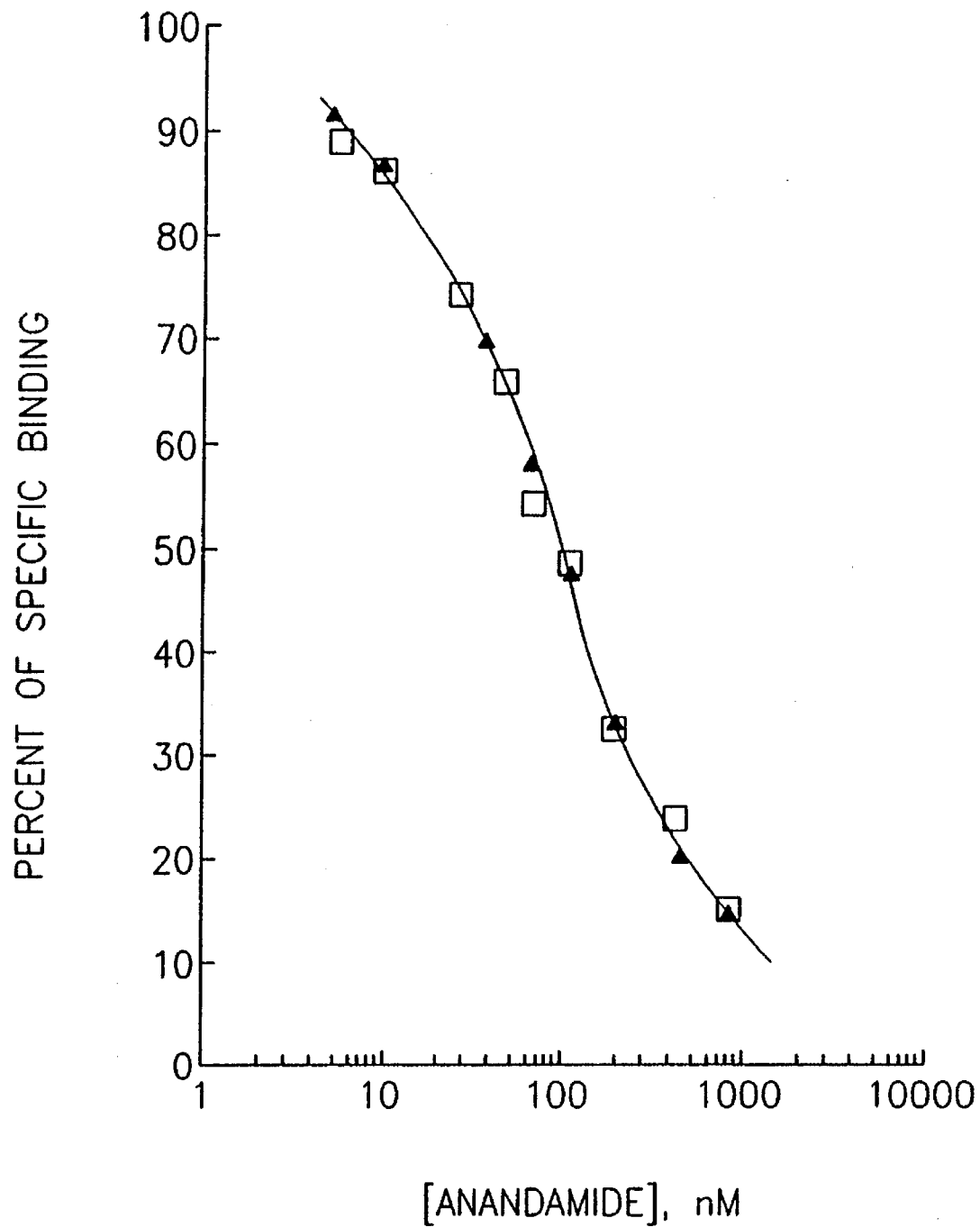
FIG. 1 illustrates the competitive inhibition of [$^3$H]HU-243 binding by natural anandamide.

FIG. 1. Competitive inhibition of [$^3$H]HU-243 binding by natural anandamide. Synaptosomal membranes were prepared from rat whole brain-minus brainstem (Sprague-Dawley males, 430–470 g). [$^3$H]HU-243 (45–55 pM) was incubated with synaptosomal membranes (protein content 3–4 μg) for 90 min at 30° C. with either the indicated concentrations of anandamide or the vehicle alone (fatty acid-free bovine serum albumin, final concentration-0.5 mg/ml). Bound and free radioligand were separated by centrifugation (see ref. 8 for full details of the assay). The data were normalized to 100% of specific binding, which was determined with 50 nM unlabeled HU-243. The amount of specific binding was 77–82% of the total radioactivity bound to the membranes. Data points (□, ▲) represent the average of triplicate determinations from two independent experiments. $K_I$ value (mean ±SE, n=3) was determined using the Ligand program; $K_I$=52 ±1.8 nM.

Figure 2:
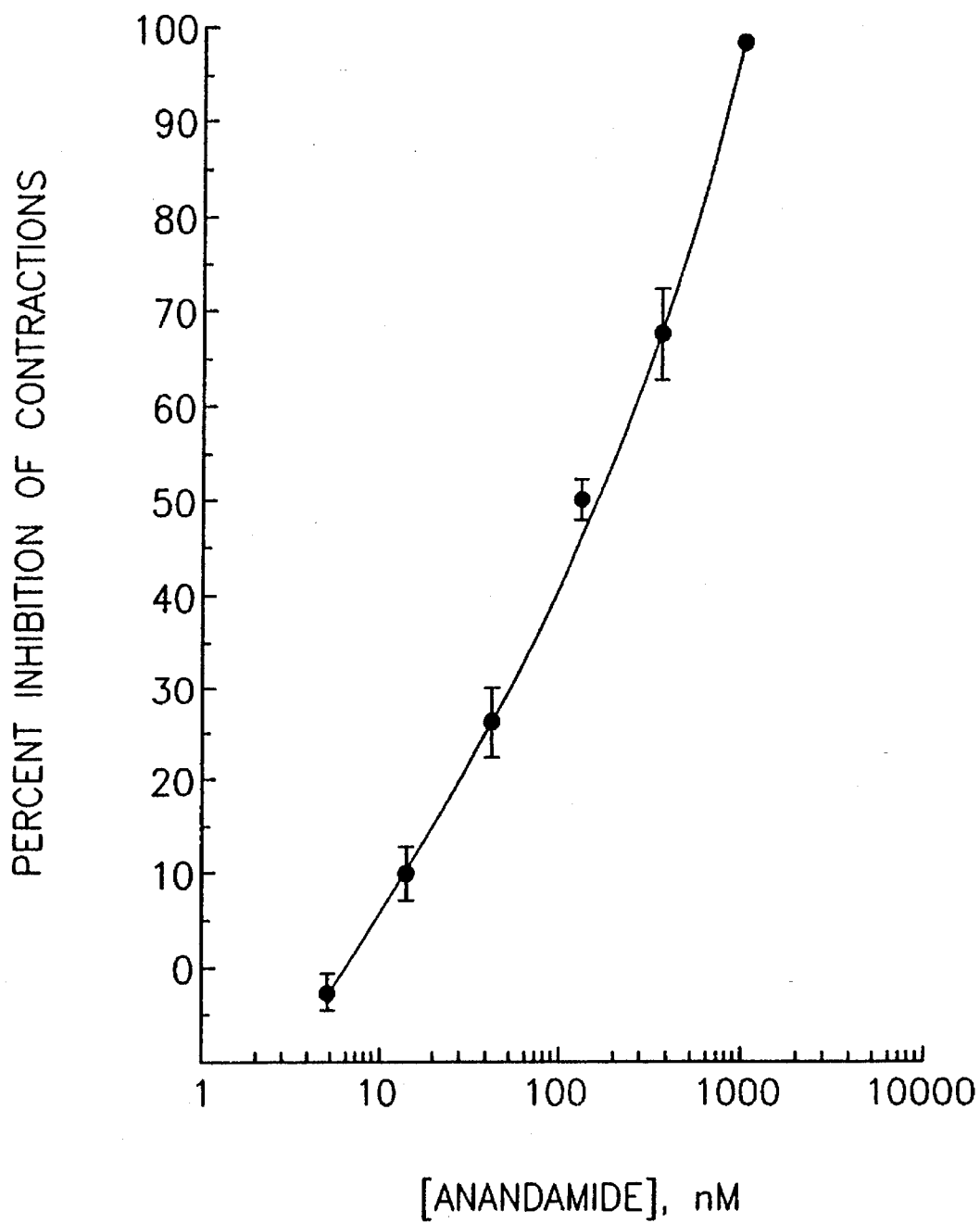
FIG. 2 illustrates inhibition of vas deferens twitch response by natural anandamide.

FIG. 2. Inhibition of vas deferens twitch response by natural anandamide. Vasa deferentia obtained from MFI mice were mounted in 4 ml siliconized organ baths under an initial tension of 0.5 g. The baths contained Mg++ -Free Krebs solution which was kept at 37 C. and bubbled with 95% $O_2$ and 5% $CO_2$. Tissues were stimulated supramaximally with 0.5 s trains of 3 pulses (train frequency 0.1 Hz: pulse duration 0.5 ms). Isometric contractions were recorded. Natural anandamide was dispersed in Tween 80 and saline (see ref. 12) and added in volumes of 40 μl. Tween 80 did not inhibit the twitch response at the maximum bath concentration used (0.63 μg/ml; n=6).

Figure 3:
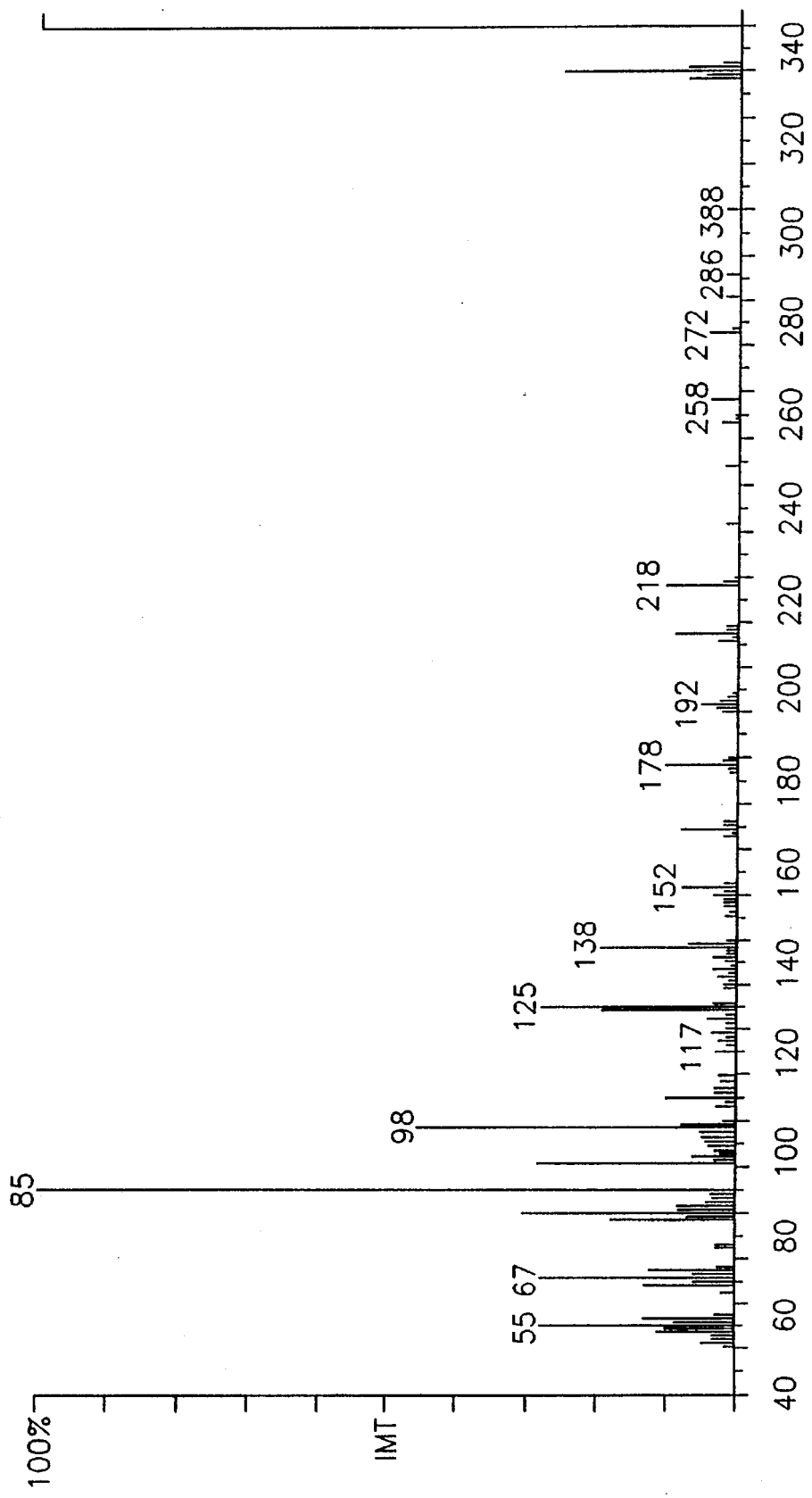
FIG. 3 is a GC-MS spectrum of anandamide.
Figure 5A:
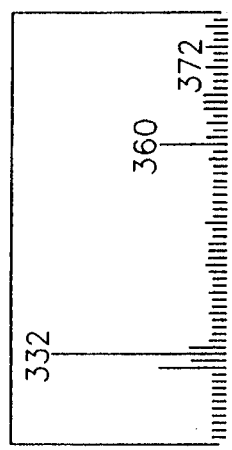
FIG. 5 EI GC-MS spectra of dehydrated homo-γ-linolenylethanolamine (5)
Figure 5B:
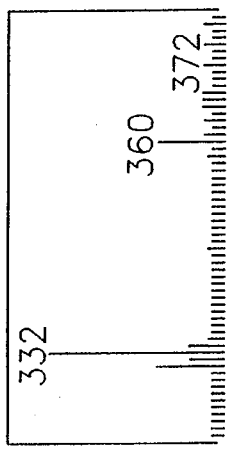
Figure 5C:
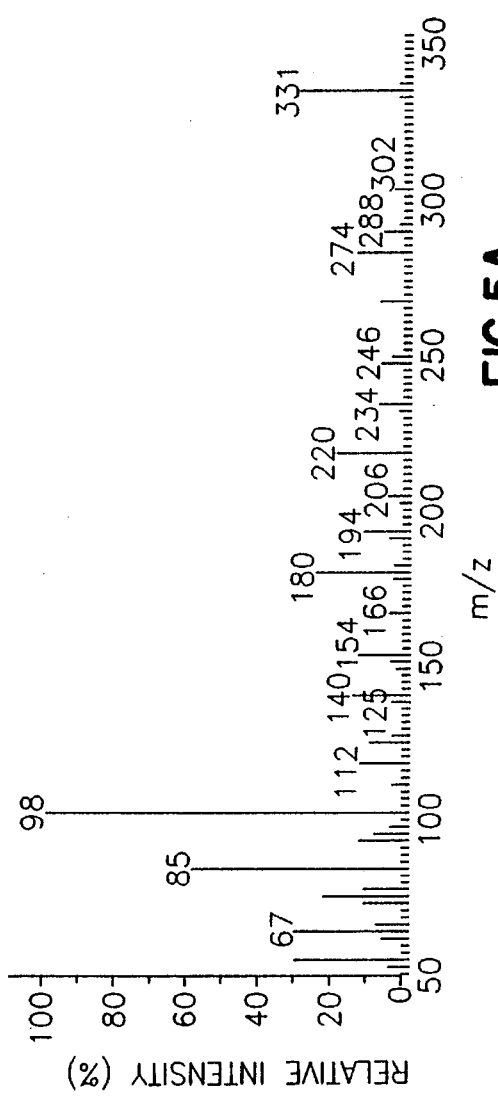
Figure 5D:
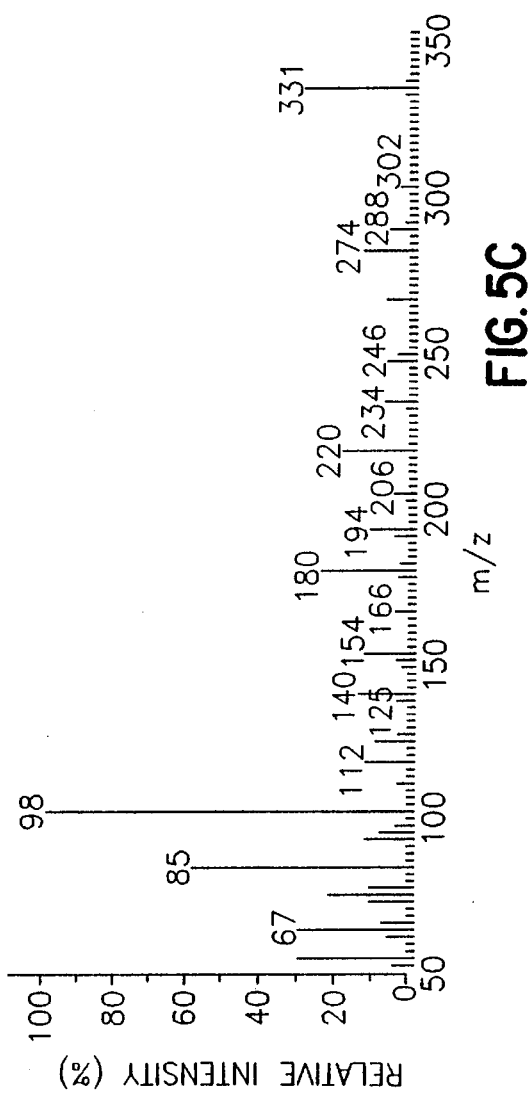
Figure 8:
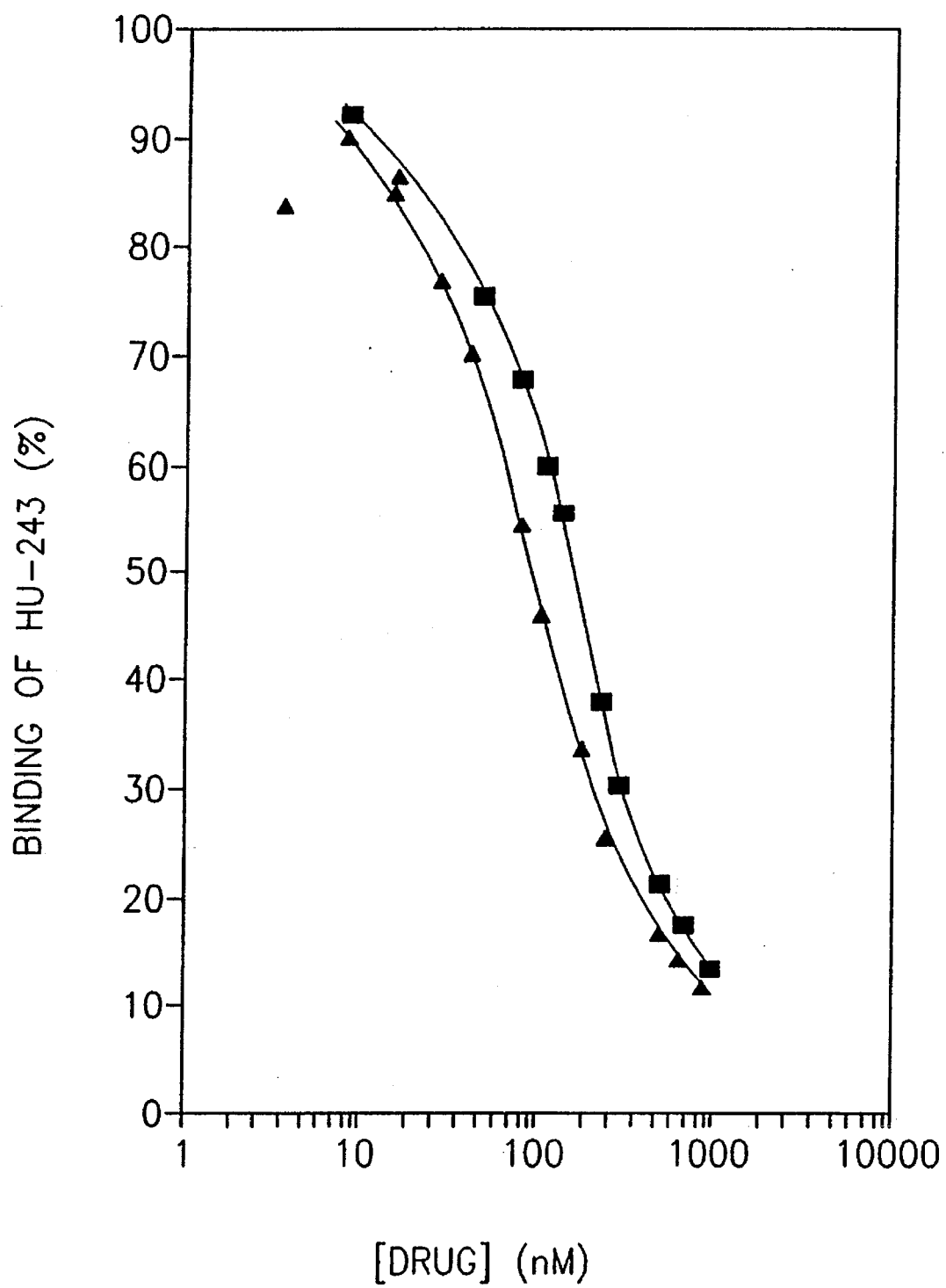
FIG. 8 illustrates competitive binding of [$^3$H]HY-243 by compound (5), squares, and by compound (6), triangles.
Figure 9A:
FIG. 9 is a Formula sheet of some compounds of the invention.
Figure 9B:
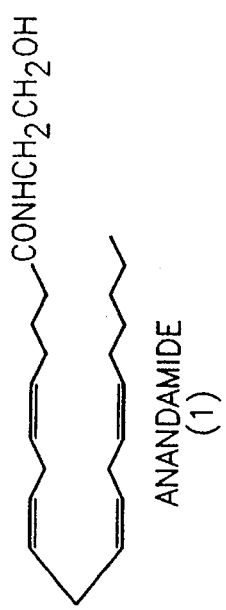
Figure 9C:
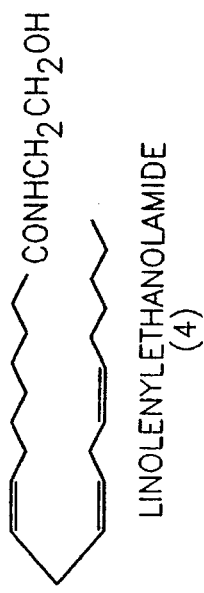
Figure 9D:
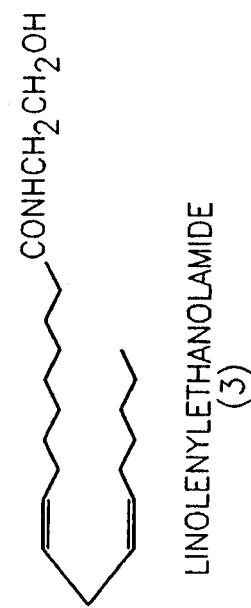
Figure 9E:
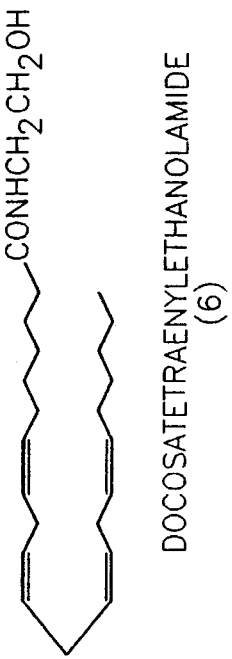
Figure 9F:
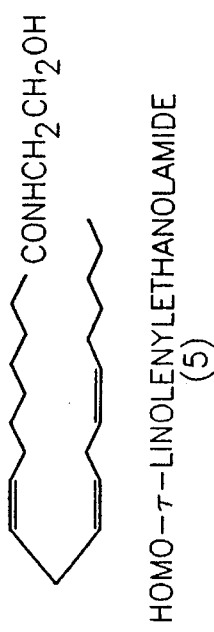

FIG. 3. GC-MS spectrum of anandamide on an ion trap instrument. Anandamide undergoes thermal dehydration under these conditions (see text) hence the above spectrum in actuality is that of the $M^+$ ion of the corresponding 2-oxazoline.

FIG. 4. Structures of anandamide and of palmitylethanolamide and of the dihydro- and tetrahydrooxazole ion fragments formed from these fatty acid ethanolamides on thermal dehydration under GC-MS conditions (see text). The m/z 112 ion is formed only from palmitylethanolamide.

| NAME OF COMPOUND | Ki |
|---|---|
| COMPOUNDS ISOLATED FROM THE BRAIN AND SYNTHESIZED. | |
| cis-7,10,13,16-docosatetraenoyl-lethanolamide | 34.4 ±3.2 nM |
| anandamide | 39.0 ±5.0 nM |
| homo-τ -linolenoylethanolamide | 53.4 ±5.5 nM |
| SYNTHETIC COMPOUNDS, PREPARED AND TESTED. | |
| N-propyl-5,8,11,14-eicosa-tetraenoylamide | 11.7 ±2.6 nM |
| N-ethyl-5,8,11,14-eicosa-tetraenoylamide | 34.0 ±2.7 nM |
| N-methyl-5,8,11,14-eicosa-tetraenoylamide | 60.0 ±7.4 nM |
| arachidonoyl-β-dimethy-lethanolamide | 161.8 ±34.1 nM |

Analysis:
Compound 5:
 Calcd for $C_{22}H_{39}NO_2$ (m.w. 349) C,75.59 H,11.25 N, 4.01 Found C,75.85 H,11.01 N, 3.88
Compound 6:
 Calcd for $C_{24}H_{41}NO_2$ (m.w. 375): C,76.75 H,11.00 N, 3.73 Found C,76.92 H,11.34 N, 3.60

Amongst these there may be mentioned anti-inflammatory, anti-asthmatic, analgetic, antiglaucoma, anti-migraine and anti-spacticity effects. They are also mood-stimulating and ameliorate the symptoms of multiple sclerosis. The unit dosage form varies according to the compound and medical use, and is generally in the range between about 1 mg to about 100 mg. The preferred range is between about 5 to about 25 mg per unit dosage form.

| Appendix II: Active Unsaturated Acylethanolamides Isolated and/or Prepared. | |
|---|---|
| Name of the compound | $K_i$ (binding to receptor) |
| cis-5,8,11,14-eicosatetraenyl ethanolamide (anandamide) from 20:4 (n-6) acid synthetic and from brain | $39.0 \pm 5$ nM |
| cis-7,10,13,16-docosatetraenylethanolamide (from 22:4 (n-6) acid) synthetic and from brain | $34.4 \pm 3.2$ nM |
| homo-γ-linolenylethanolamide (cis-8,11,14-eicosatrienylethanolamide) (from cis-8,11,14-eicosatrienoic acid) 20:3 (n-6) synthetic and from brain | $53.4 \pm 5.5$ nM |
| cis-4,7,10,13,16,19-docosahexaenylethanolamide from 22:6 (n-3) acid | 328.9 nM |
| cis-11,14-eicosadienylethanolamide from 20:2 (n-6) acid | 1.5 μM |
| γ-linolenylethanolamide (cis-6,9,12-octadecatrienylethanolamide) (from cis-6,9,12-octadecatrienoic acid) 18:3 (n-6) | $4.6 \pm 0.3$ μM |

Pharmaceutical compositions, containing as active ingredient an effective quantity of the compounds of the present invention, have a variety of pharmacological effects.

REFERENCES

1. Devane, W. A. et al., Hanus, L.; Breuer, A.; Pertwee, R. G.; Stevenson, L. A.; Griffin, G.; Gibson, D.; Mandelbaum, A.; Etinger, A.; Mechoulam, R. Isolation and Structure of a Brain Constituent that Binds to the Cannabinoid Receptor. *Science*, 1992, 258, 1946–1949;

3. Vogel, Z.; Barg, J.; Levy, R.; Saya, D.; Heldman, E.; Mechoulam, R. Anandamide, a Brain Endogenous Compound, Interacts Specifically with Cannabinoid Receptors and Inhibits Adenylate Cyclase. *J. Neurochem.* (in press);

4. Bachur, N. R.; Masek, K.; Melmon, K. L.; Udenfriend, S. Fatty Acid Amides of Ethanolamine in Mammalian Tissues. *J. Biol. Chem.* 1965, 240, 1019–1024;

5. Agranoff, B. W. In *Basic Neurochemistry;* Seigel, G., Agranoff, B., Albers, R. W., Molinoff, P., Eds; Raven Press: New York, 1989;

6. Devane, W. A. et al., Breuer, A.; Jarbe, T. U. C.; Eisen, M.; Mechoulam, R. A Novel Probe for the Cannabinoid Receptor. *J. Med. Chem.* 1992, 35, 2065–2069.

We claim:

1. Essentially pure compounds off the general formula

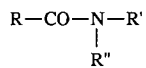

wherein R is the alkenyl moiety of a polyunsaturated fatty acid of 16 to 28 carbon atoms, with 2 to 6 double bonds, with the first double bond at the C-6, or C-9 position, counting from the non-carboxyl part of the molecule, where R" is selected from —H, lower-alkyl, —OH and —$(CH_2)_n$—OH, where n is a small integer, and when R" is hydrogen, R' is selected from lower alkyl, and —$(CH_2)_m$OH, where m is a small integer, when R" is lower-alkyl, R" is —$(CH_2)_p$—OH, where p is a small integer, when R" is —OH, R' is —$(CH_2)_q$—OH where q is a small integer, or both R' and R" are each —$(CH_2)_n$—OH, where n is a small integer, and acid addition salts and complexes of these.

2. A compound according to claim 1, where the alkenyl moiety is an octadecadienoic, octadecatrienoic, eicosapentaenoic, docosahexaenoic, eicosatrienoic or eicosatetraenoic moiety.

3. A compound according to claim 1, selected from arachidonylethanolamide, cis-7,10,13,16-docosatetraenoylethanolamide, homo-δ-linolenoylethanolamide, N-propyl 5,8,11,14-eicosatetraenoylamide, N-ethyl-5,8-11, 14-eicosatetraenoylamide, N-methyl-5,8,11,14 eicosatetraenoylamide and arachidonoyl-β-dimethylethanolamide.

4. An antiinflammatory, anti-asthmatic, analgetic, antiemetic, antiglaucoma, anti-migraine, anti-spasticity, mood stimulating and symptoms of multiple sclerosis ameliorating pharmaceutical composition, which contains as active ingredient an effective quantity of a compound defined in claim 1.

5. A composition according to claim 4, where the active ingredient is a compound selected from arachidonylethanolamide, cis-7,10,13,16-docosatetraenoylethanolamide, homo-δ-linolenoylethanolamide, N-propyl 5,8,11,14-eicosatetraenoylamide, N-ethyl-5,8-11,14-eicosatetraenoylamide, N-methyl-5,8,11,14 eicosatetraenoylamide and arachidonoyl-β-dimethylethanolamide.

6. A composition according to claim 4, where the unit dosage for human administration is from about 1 mg to about 100 mg of the active compound.

7. A compound of claim 1, in radioactive tagged form.

8. A compound according to claim 7, where the tag is $^3H$ or $^{14}C$.

9. A composition for binding to the cannabinoid receptor in brain, comprising an effective quantity of a compound of the general formula

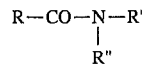

wherein R is the alkenyl moiety of a polyunsaturated fatty acid of 16 to 28 carbon atoms, with 2 to 6 double bonds, with the first double bond at the C-3, C-6, or C-9 position, counting from the non-carboxyl part of the molecule, where R" is selected from —H, lower-alkyl, —OH and —$(CH_2)_n$—OH, where n is a small integer, and when R" is hydrogen, R' is selected form lower alkyl, and —$(CH_2)_m$OH, where m is a small integer, when R" is lower-alkyl, R' is —$(CH_2)_p$—OH, where p is a small integer, when R" is —OH, R' is —$(CH_2)_q$—OH where q is a small integer, or both R' and R" are each —$(CH_2)_n$—OH, where n is a small integer, and acid addition salts and complexes of these.

* * * * *